(12) United States Patent
Ward et al.

(10) Patent No.: US 9,056,171 B2
(45) Date of Patent: Jun. 16, 2015

(54) ARTERIOVENOUS SHUNT HAVING ECCENTRIC ANCHOR STENT

(75) Inventors: Sean Ward, Castleknock (IE); Gerry McCaffrey, Tuam (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 636 days.

(21) Appl. No.: 13/404,477

(22) Filed: Feb. 24, 2012

(65) Prior Publication Data

US 2013/0226067 A1    Aug. 29, 2013

(51) Int. Cl.
| | | |
|---|---|---|
| *A61M 5/00* | (2006.01) | |
| *A61M 1/36* | (2006.01) | |
| *A61F 2/07* | (2013.01) | |
| *A61F 2/06* | (2013.01) | |

(52) U.S. Cl.
CPC ............... *A61M 1/3655* (2013.01); *A61F 2/07* (2013.01); *A61F 2002/061* (2013.01)

(58) Field of Classification Search
CPC ......... A61M 1/3655; A61F 2002/061
USPC .......... 604/8, 9, 174, 175, 264; 623/1.11, 1.3, 623/1.31, 1.36, 1.37, 23.64, 23.7; 606/196, 606/198, 191, 153–158
See application file for complete search history.

(56) References Cited

U.S. PATENT DOCUMENTS

| | | | |
|---|---|---|---|
| 6,010,529 A * | 1/2000 | Herweck et al. ........... 623/23.69 |
| 6,432,127 B1 * | 8/2002 | Kim et al. .................... 623/1.11 |
| 6,517,558 B2 | 2/2003 | Gittings et al. |
| 6,746,464 B1 | 6/2004 | Makower |
| 2002/0058897 A1 | 5/2002 | Renati |
| 2003/0088256 A1 | 5/2003 | Conston et al. |
| 2010/0056978 A1 * | 3/2010 | Machan et al. .................... 604/9 |
| 2010/0286705 A1 * | 11/2010 | Vassiliades, Jr. .............. 606/108 |
| 2012/0065652 A1 * | 3/2012 | Cully et al. .................... 606/153 |

* cited by examiner

*Primary Examiner* — Philip R Wiest
*Assistant Examiner* — Ariana Zimbouski

(57) ABSTRACT

An arteriovenous shunt includes a self-expanding stent graft having a self-expanding anchor stent mounted eccentrically and externally about at least one end segment of the stent graft. A fluid passageway extends between open first and second ends of the shunt. The anchor stent has an expanded diameter greater than an expanded diameter of the stent graft. The expanded diameter of the stent graft is smaller than the artery or vein into which it is deployed. Methods of deploying the arteriovenous shunt are also disclosed.

9 Claims, 6 Drawing Sheets

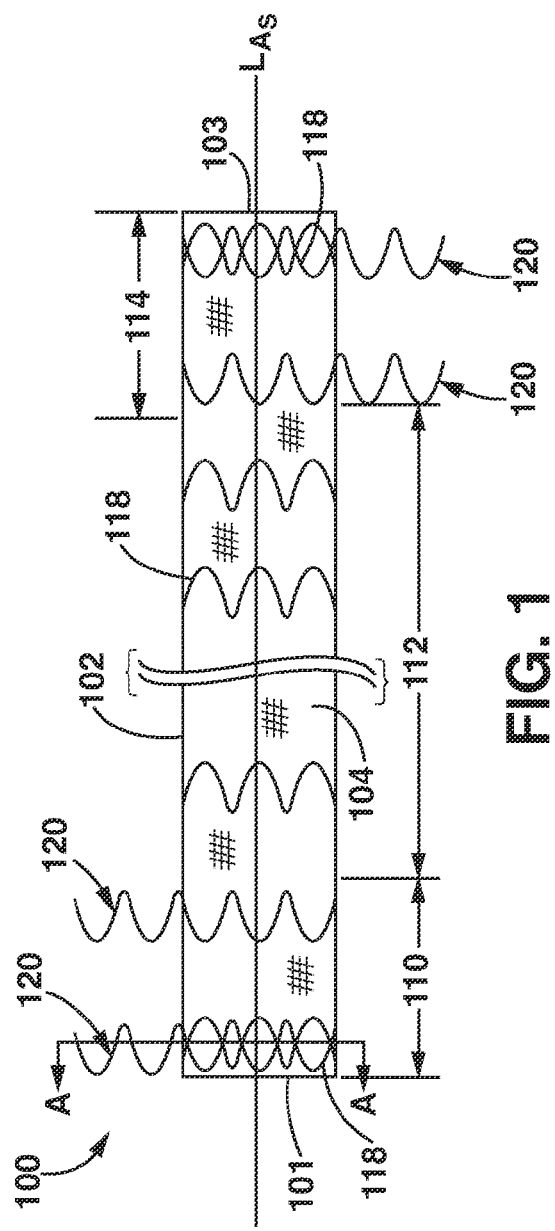
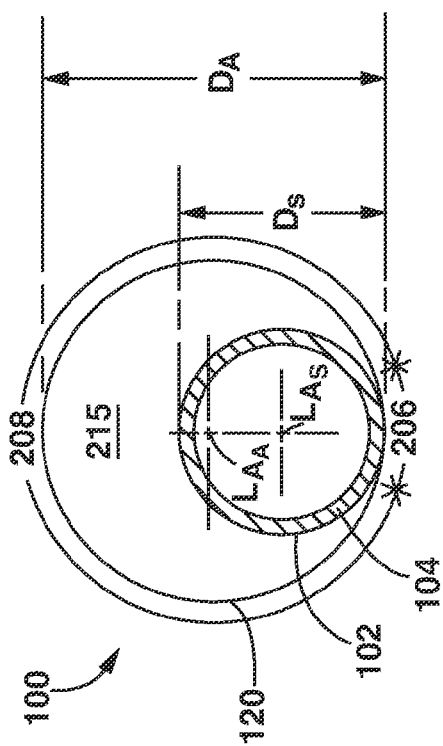
FIG. 1
FIG. 2

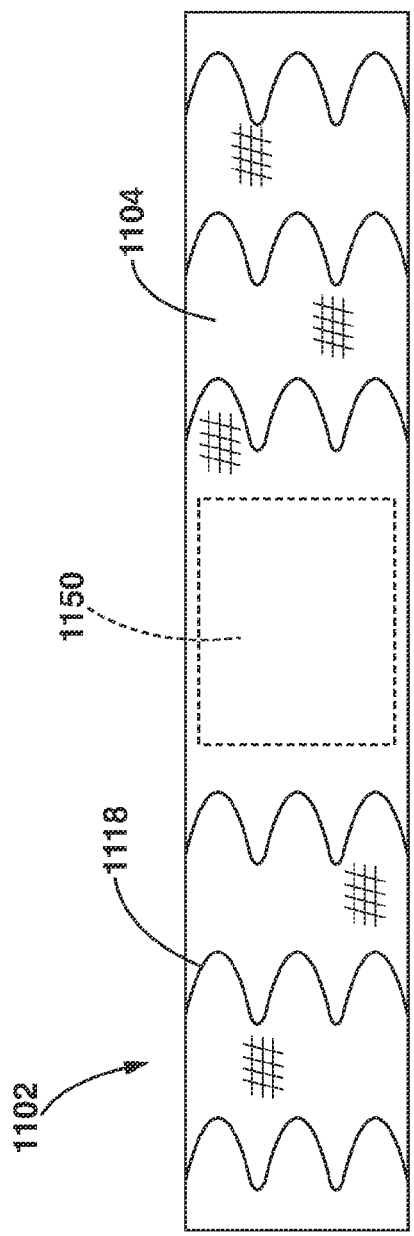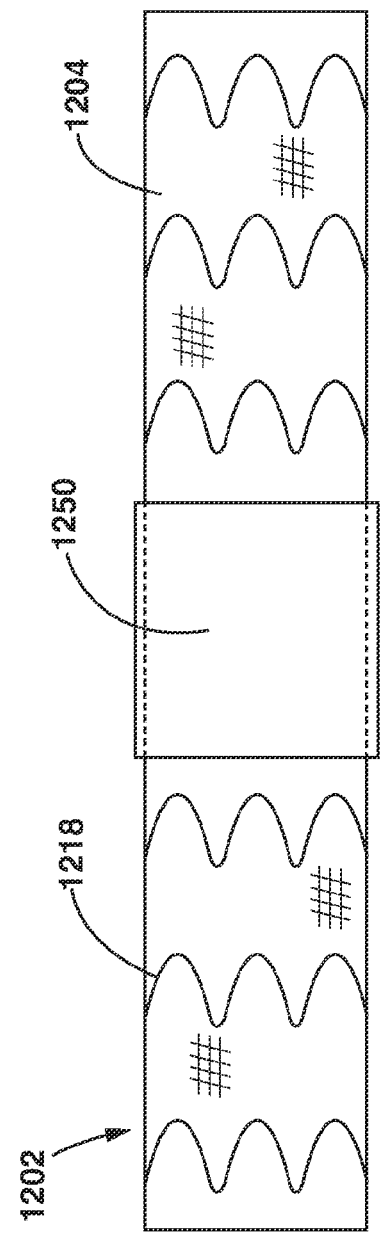

ARTERIOVENOUS SHUNT HAVING ECCENTRIC ANCHOR STENT

FIELD OF THE INVENTION

The invention relates to an implantable arteriovenous (AV) shunt having an anchor stent eccentrically and externally mounted about at least one end thereof.

BACKGROUND OF THE INVENTION

In modern medicine there are numerous treatment situations in which it is desirable to create shunts or flow-through connections between blood vessels and/or other anatomical structures of the body. Such treatments include, for example, hemodialysis, hemofiltration, hemodiafiltration, plasmapheresis, and extracorporeal membrane oxygenation (ECMO). In many cases, open surgical techniques have been used to form anatomic connections or fistulas between adjacent vessels of body structures. More recently, percutaneous catheter-based techniques and devices have been developed for creating channels or passageway's (i.e., shunts) between adjacent vessels or anatomical structures.

In addition to the above-listed treatments, arteriovenous (AV) shunt devices have been proposed for treating chronic obstructive pulmonary disease (COPD) and drug-resistant hypertension. COPD, also called chronic obstructive airway disease, is a syndrome that may be caused by a number of different diseases, all of which damage the alveoli and bronchioles, leading to impaired lung function. These diseases include asthmatic bronchitis, chronic bronchitis (with normal airflow), chronic obstructive bronchitis, and emphysema. As the alveoli and bronchial tubes are destroyed, the remaining healthy lung tissue must work harder to provide the required amount of blood oxygenation. The need for more air leads to lung over-inflation. As the lung over-expands, it gradually enlarges, completely filling the chest cavity and causing a sense of shortness of breath. The lung eventually loses its elasticity and the combination of a larger, less elastic lung and damaged, nonfunctioning tissue leads to slower airflow into and out of the lung, resulting in the feeling in the patient of an obstructed airway.

One manner of treating COPD is oxygen therapy, which requires a patient to remain near a stationary oxygen source or carry a bulky portable oxygen source when away from home or a treatment facility. Understandably such oxygen therapy has many disadvantages. One surgical treatment that has been proposed for treating patients with COPD is lung reduction surgery. Such surgery, however, can be used on only a small percentage of the total patient population, requires long recovery times, and does not always provide a clear patient benefit.

Arteriovenous (AV) shunt devices for treating COPD provide a fistula between an artery and a vein that are anatomically parallel to each other. The approach is to create an arteriovenous fistula by implanting a shunt-like device between two major blood vessels in, for example, the leg, thus utilizing cardiovascular reserve to overcome respiratory insufficiency and improve oxygenation to the lungs. The shunt allows oxygen-rich blood from the artery to flow to the vein and thereby increases the oxygen content of the blood returning to the heart and lungs, which in turn is considered to benefit a patient suffering from COPD. The implantation of the shunt can increase cardiac output by about one liter per minute, without impacting heart rate or oxygen consumptions.

Such shunt devices have been suggested to be implanted via an open surgical procedure or via a minimally invasive intravascular catheterization procedure, depending on the specific arterial and venous locations that are to be connected by the AV shunt. A need continues to exist in the art for an AV shunt that may be quickly and simply delivered, deployed, and secured in place via a minimally invasive intravascular procedure. In addition, a need continues to exist in the art for an AV shunt that directs blood flow into and out of the fluid passageway of the shunt.

BRIEF SUMMARY OF THE INVENTION

Embodiments hereof relate to an arteriovenous shunt assembly that includes a self-expanding stent graft having a self-expanding anchor stent mounted eccentrically and externally about at least one end segment of the stent graft. A fluid passageway extends between open first and second ends of the shunt assembly. The anchor stent has an expanded diameter greater than an expanded diameter of the stent graft. The ends of the stent graft are smaller in diameter than the blood vessel lumens into which they are deployed such that, while some blood is diverted from the artery to the vein via the shunt, a portion of the blood in the artery and all of the blood in the vein flows past the shunt to continue downstream.

In one embodiment, each anchor stem includes a portion of an inner surface coupled to a portion of an exterior surface of the stent graft. In another embodiment, each anchor stent includes a self-expanding tubular body with a side opening that is sized to receive the tubular shunt therethrough, and a retainer ring sized to receive and secure the tubular shunt against one side of the bore within the stent anchor.

Embodiments hereof also relate to a method for forming a fluid connection between a first body vessel and a second body vessel. A shunt assembly is intravascularly delivered in its collapsed configuration to a tissue tract formed between the first vessel to the second vessel. The shunt assembly includes a tubular shunt and a self-expanding anchor stent coupled eccentrically and externally to each of a first and second end segment of the tubular shunt. Each of the anchor stents has an expanded diameter greater than an expanded diameter of the tubular shunt. The tubular shunt is positioned to extend through the tissue tract such that the first end segment of the tubular shunt is disposed in the first vessel and extends parallel to the vessel wall, and the second end segment of the tubular shunt is disposed in the second vessel and extends parallel to the vessel wall. Each anchor stent is radially expanded into wall apposition spanning a body vessel such that a longitudinal axis of a first shunt end segment is parallel to and radially offset from a longitudinal axis of the anchor stent. The shunt end segment does not span or fully occupy the body vessel, thus permitting a portion of the blood in each vessel to flow past the shunt.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is a side view of an arteriovenous (AV) shunt assembly according to an embodiment hereof, wherein the IV shunt assembly includes a tubular shunt and anchor stents coupled to end segments thereof.

FIG. 2 is a cross-sectional view taken along line A-A of FIG. 1.

FIG. 11 is a side view of an AV shunt for use in embodiments described herein, wherein the AV shunt includes a valve therein for selectively adjusting flow through the shunt.

FIG. 12 is a side view of another AV shunt for use in embodiments described herein, wherein the AV shunt includes a valve around the outer surface of the shunt for selectively adjusting flow there through.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. In addition, the term "self-expanding" is used in the following description with respect to a material that has a mechanical memory to return to an expanded deployed configuration from a compressed or constrained delivery configuration. Non-exhaustive exemplary self-expanding materials include stainless steel, a pseudo-elastic metal such as a nickel titanium alloy (nitinol), a polymer, or a so-called super alloy, which may have a base metal of nickel, cobalt, chromium, or other metal. Mechanical memory may be imparted to a wire or tubular structure by thermal treatment to achieve a spring temper in stainless steel, for example, or to meta shape memory in a susceptible metal alloy, such as nitinol, or a polymer such as any of the polymers disclosed in U.S. Pat. Appl. Pub. No. 2004/0111111 to Lin, which is incorporated by reference herein in its entirety.

The following detailed description is merely exemplary in nature and is not intended to limit the invention or the application and uses of the invention. Although the description of the invention is in the context of an AV shunt for the treatment of a patient suffering from COPD and related conditions, embodiments hereof may also be used as a shunt for treatment of other conditions and/or may be used to bridge any anatomical lumens or conduits where it is deemed useful. Furthermore, there is no intention to be bound by any expressed or implied theory presented in the preceding technical field, background, brief summary or the following detailed description.

Figure 6:
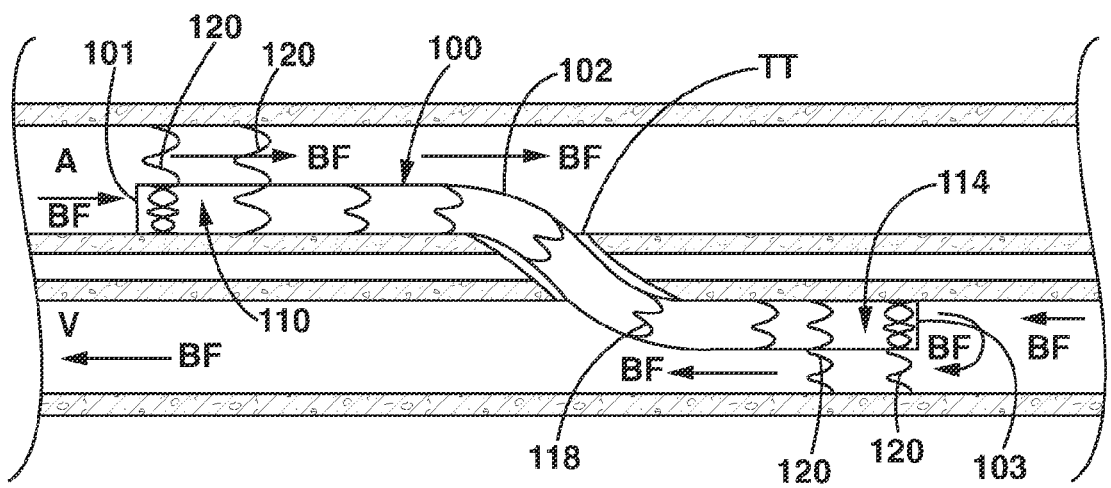
Figure 10:
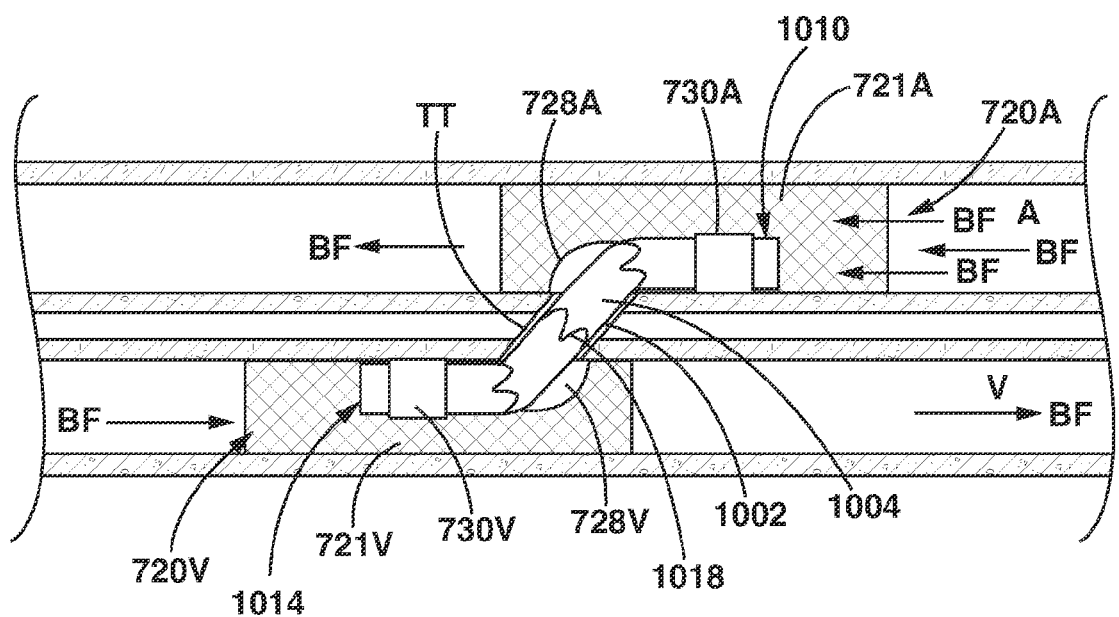
FIG. 10 is a side view of anchor stents of FIG. 7 disposed in adjacent vessels, and an AV shunt positioned and secured through the anchor stents.

Embodiments hereof relate to anchoring components for an arteriovenous (AV) shunt. In particular, referring to FIGS. 1 and 2, an AV shunt assembly 100 includes a tubular shunt 102 and anchor stents 120. Tubular shunt 102 is a cylindrical component that defines a fluid passageway 216 there through. Tubular shunt 102 has a longitudinal axis $LA_S$ and includes a first end or arterial segment 110 configured for placement in an artery, a second end or vein segment 114 configured for placement in a vein, and an intermediate or coupling portion 112 between first and second end segments 110, 114 for extending through a tissue tract between the artery and the vein. A pair of self-expanding anchor stents 120 is eccentrically and externally mounted about each of first and second end segments 110, 114 of tubular shunt 102. Although FIG. 1 shows two longitudinally spaced apart anchor stents 120 attached to each end segment, only one anchor stent at each end segment is required and a greater number of anchor stents may be utilized depending upon the length of each end segment. Further, while at least one anchor stent is required at each end segment, it will be understood by those of ordinary skill in the art that an equal number of anchor stents is not required around first and second end segments 110, 114. For example, an embodiment may include a first shunt end portion 110 surrounded by a single anchor stent 120 while second shunt end portion 114 is surrounded by a pair of anchor stents 120. The expanded diameter $D_S$ of shunt 102 is less than the lumen diameter of either blood vessel into which it is to be deployed such that a portion of the blood in the artery and all of the blood in the vein flows past the shunt to continue downstream in the respective vessel. Each anchor stent 120 has an expanded diameter $D_A$ that is greater than an expanded diameter $D_S$ of shunt 102 and is equal to or greater than a luminal diameter of a vessel in which the anchor stent is to be deployed as will be explained in more detail herein. In an embodiment, expanded diameter $D_S$ of shunt 102 is between 25% and 75% of expanded anchor stent diameter $D_A$. In one embodiment, expanded diameter $D_S$ of shunt 102 is approximately 50% of expanded anchor stent diameter $D_A$. In the expanded configuration of AV shunt assembly 100 illustrated in FIGS. 1 and 2, anchor stents 120 around first end segment 110 extend beyond a first or top surface of tubular shunt 102 and anchor stents 120 around second end segment 114 extend beyond an opposing or bottom surface of tubular shunt 102. When anchor stents 120 are deployed or expanded within a body lumen, the longitudinal axis $LA_S$ of first shunt end segment 110 is parallel to and radially offset from a longitudinal axis $LA_A$ of its respective anchor stent 120. The longitudinal axis $LA_S$ of second shunt end segment 114 is also parallel to and radially offset from the longitudinal axis $LA_A$ of its respective anchor stent 120. However, first and second shunt end segments 110, 114 are radially offset in different, preferably opposite directions. Due to being radially offset in opposite directions, first and second shunt end segments 110, 114 are pushed toward each other to sit against adjacent walls of adjacent vessels, as shown in FIGS. 6 and 10. It will be understood by one of ordinary skill in the art that the terms "top" and "bottom" as used herein are relative terms used for illustrative purposes only.

As will be explained in more detail herein, anchor stents 120 expand in situ into apposition with the inner walls of the artery and the vein, and orient first and second end segments 110, 114 of tubular shunt 102 to extend parallel to walls of the artery and vein, respectively. Orienting shunt end segments 110, 114 to longitudinally extend within the artery and vein, respectively, beneficially directs the fluid flow into an inflow end 101 and out of an outflow end 103 of the fluid passageway of the shunt and thus serves to improve the hemodynamics of blood flow through the shunt. In addition, since tubular shunt 102 has an expanded diameter smaller than anchor stents 120 and smaller than the lumens of the blood vessels, the shunt diverts only some of the blood flowing within the artery to the vein. Such partial diversion ensures that sufficient oxygenated blood is supplied via the artery to tissue downstream of the shunt. All of the blood in the vein, including additional oxygenated blood received through the shunt continues to flow back to the heart with only minor obstruction by shunt end segment 114. Furthermore, having the shunt end segments 110, 114 radially positioned against the walls of the vessels that are adjacent to each other, i.e. against the vessel walls near the respective ends of tissue tract TT, avoids having shunt 102 extend laterally across the blood vessel lumens and disturbing the blood flow therethrough.

Tubular shunt 102 is a collapsible stent graft including graft material 104 having a plurality of radially compressible annular support stents 118 attached thereto. FIG. 1 illustrates seven support stents 118 attached to graft material 104; However, a greater or lesser number of stents may be utilized. Cylindrical support stents 118 are biased in a radially outward direction to expanded diameter $D_S$ and may be of known stem constructions such as laser-cut or etched tubes or sinusoidal patterned wireforms. Support stents 118 are formed from a self-expanding elastic or superelastic material, such as a nickel-titanium (nitinol) alloy, to return to an expanded deployed configuration from a compressed or constrained delivery configuration as described for example, in U.S. Pat. No. 5,713,917 and U.S. Pat. No. 5,824,041, which are incorporated by reference herein in their entirety. Stents 118 may be attached or mechanically coupled to graft material 104 by various means, such as, for example, by suturing onto either the inside or outside of graft material 104. Although shown as coupled to an exterior surface of graft material 104, stents 118 may alternatively be coupled to an interior surface of graft material 104. Further, although steins 118 are shown in FIG. 1 as a plurality of individual wire rings, it will be understood by one of ordinary skill in the art that the support stents 118 may have various other configurations that are suitable for forming a fluid connection between an artery and an adjacent vein. For example, tubular shunt 102 may include a stent graft having a continuous tubular stent framework, e.g., a mesh or lattice scaffolding, attached to graft material 104.

Graft material 104 creates a conduit or fluid passageway when attached to support stents 118. Graft material 104 may be expanded polytetrafluoroethylene (ePTFE) or a low-porosity knit or woven polyester fabric, either of which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example. In another embodiment, graft material 104 could also be a natural material such as pericardium or another membranous tissue such as intestinal submucosa.

Anchor stents 120 are similar in structure to stents 118, but as previously described have an expanded diameter $D_A$ that is greater than expanded diameter $D_S$ of support stents 118 of shunt 102. Cylindrical anchor stents 120 are radially compressible and may be of known stent constructions such as laser-cut or etched tubes or wavelike or sinusoidal patterned wire rings that define a cylindrical bore 215. Each anchor stent 120 is biased to expanded diameter $D_A$ which is sized such that anchor stents 120 expand into apposition with interior walls of the target vessels to be connected, i.e., an artery and adjacent vein. Although adjacent segments of arteries and veins targeted for shunting typically have similar lumen diameters, the invention can be modified to suit anatomic variations having different lumen diameters by providing an AV shunt assembly with anchor stent diameters $D_A$ being sized differently to fit their respective target vessels. Additionally, the expanded diameter $D_S$ of support stents 118 of shunt 102 can be sized to ensure that they are smaller than the blood vessel lumens into which they are intended to be implanted, thus assuring that shunt 102 only redirects a portion of the blood flowing through the shunted vessels. Anchor stents 120 are formed from a self-expanding elastic or superelastic material, such as a nickel-titanium alloy (nitinol), to return to an expanded deployed configuration from a compressed or constrained delivery configuration.

As shown in FIG. 2, only a portion of each anchor stent 120, i.e., a first circumferential portion 206, is tangentially coupled to tubular shunt 102 along shunt end segment 110, 114 via stitching, suturing, or other mechanical method. The remaining portion of each anchor stent 120, i.e., a second circumferential portion 208, is detached from tubular shunt 102. Second circumferential portion 208 is greater than first inner circumferential portion 206 because anchor stent diameter $D_A$ is larger than shunt diameter $D_S$. When expanded, circumferential portion 208 functions to radially offset anchor stent 120 and tubular shunt 102 as apparent from the spaced apart locations of longitudinal axis $LA_S$ of tubular shunt 102 and longitudinal axis $LA_A$ of anchor stent 120. In situ, circumferential portion 208 pushes or positions shunt 102 against one side of the target vessel, i.e., the artery or the vein, to allow some blood to flow unobstructed within the target vessel through bore 215 of anchor stein 120, thereby bypassing or avoiding shunt 102. The offsetting feature of anchor stents 120 that intentionally allow some blood to bypass the inlet or outlet of shunt 102 is different from known stent grafts having anchor stents that are intended to aid in forming a circumferential seal with the blood vessel wall at both ends of the stent graft, thereby directing all blood through the conventional stent graft. Although FIG. 2 is a cross-sectional view taken within first end segment 110 of tubular shunt 102, it will be understood by one of ordinary skill in the art that anchor stents 120 coupled to second end segment 114 may be identical to anchor stents 120 coupled to first end segment 110 except for the opposite orientation of first and second inner circumferential portions 206, 208. With respect to anchor stents 120 coupled to second end segment 114, the second inner circumferential portion 208 of anchor stents 120 extends below the second or bottom surface of the tubular shunt.

In an embodiment, first and second end segments 110, 114 include at least one stent 118 adjacent to each of inflow and outflow ends 101,103 to ensure that the ends of tubular shunt 102 are open and prevented from collapsing. The at least one support stent 118 may overlap an anchor stent 120, as shown in FIG. 1, or may be positioned adjacent to the anchor stent. For example, the at least one support stent 118 may be positioned between two longitudinally spaced apart anchor stents 120 at each end segment of tubular shunt 102.

FIGS. 3-6 illustrate a method of forming a connection between an artery A and an adjacent vein V with AV shunt assembly 100. Blood flow BF is indicated in the figures with directional arrows. In one embodiment, artery A and vein V are the femoral artery and femoral vein of a patient's leg. However, embodiments hereof may be deployed in any two adjacent body lumens or cavities in which it is desirable to form a fluid connection there between.

Figure 3:
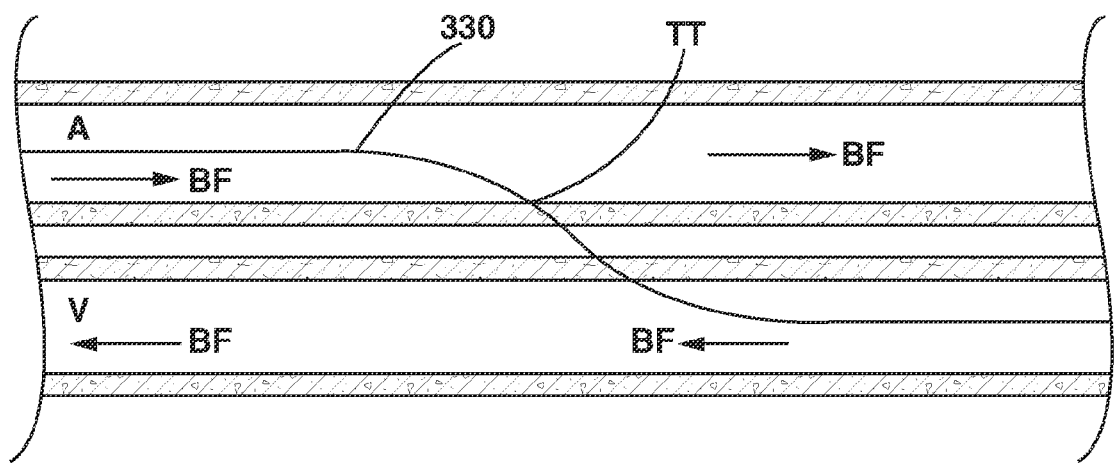
FIGS. 3-6 illustrate a method of forming a connection between an artery and adjacent vein using the AV shunt assembly of FIG. 1.

With reference to FIG. 3, a guidewire 330 is shown after having been percutaneously introduced via, e.g. the Seldinger technique, into the arterial vasculature. Guidewire 330 is tracked to a target location in the femoral artery at which an AV fistula or connection is to be formed. Using known minimally invasive penetrating devices, as mentioned elsewhere herein, punctures are created to form tissue tract TT extending through the wall of artery A, through any intervening tissue and/or hollow space between vein V and artery A, and through the wall of vein V to thereby extend between the lumens of vein V and artery A. Guidewire 330 is advanced through tissue tract TT.

Figure 4:
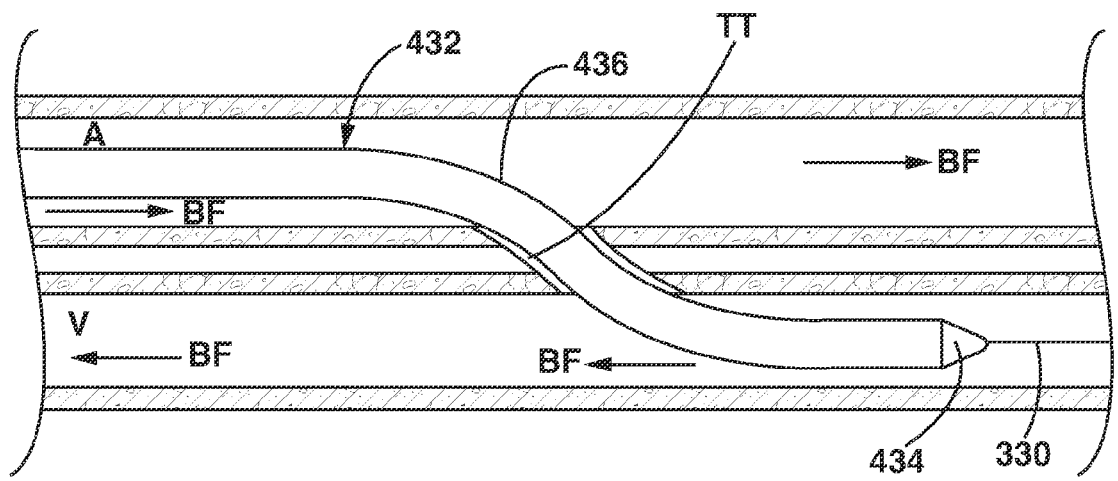
Figure 5:
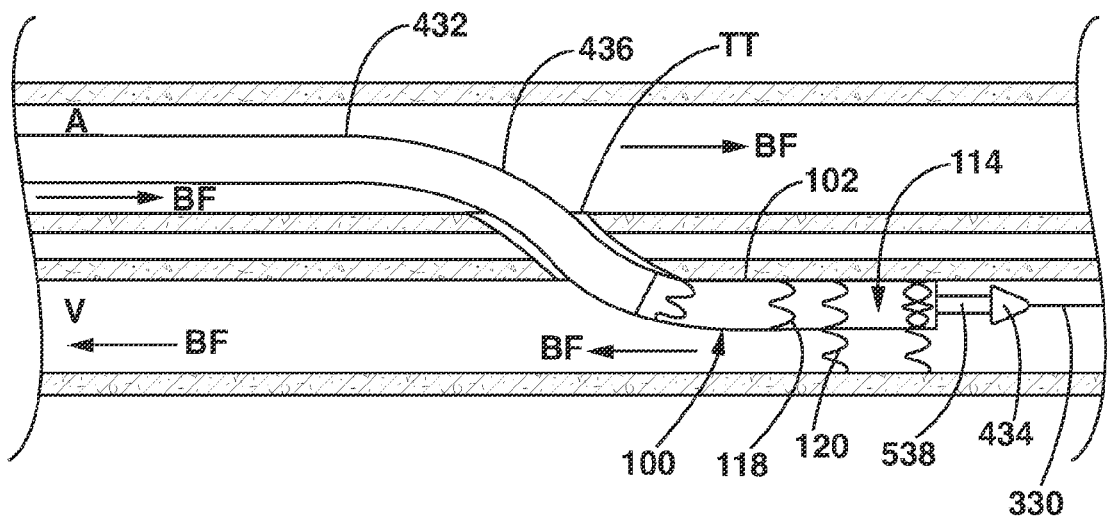

In FIG. 4, an AV shunt delivery system 432 is shown after having been introduced into the vasculature and tracked over guidewire 330 through tissue track TT. Delivery system 432 may be modified to create tissue tract TT, or tissue tract TT may have been previously formed by a separate tissue penetrating catheter device (not shown) as would be known to one of skill in the art. The PIONEER catheter, commercially available from Medtronic CardioVascular, Inc., Santa Rosa, Calif., is a tissue penetrating catheter suitable for use in embodiments described herein for forming tissue track TT. Optionally, in some applications of this method, one or more tract modifying devices such as balloon catheters and/or atherectomy catheters may be used to enlarge, debulk, and/or bore the tissue tract TT, after which they are removed. Examples of tract modifying devices and procedures of this sort are provided in U.S. Pat. No. 5,830,222 to Makower and U.S. Pat. No. 6,561,998 to Roth et al., the disclosures of which are hereby incorporated by reference herein in their entireties. For illustrative purposes only, tissue tract TT is shown in FIGS. 4 and 5 as being large enough to have delivery system 432 fit loosely therein. During actual use, the fit between delivery system 432 and tissue tract TT is tight enough to substantially seal the vessel wall punctures at both ends of tract TT against interstitial blood leakage.

AV shunt delivery system 432 includes an outer retractable sheath 436 and a catheter 538 (shown in FIG. 5) having a tapered distal end 434. AV shunt assembly 100 is mounted about the distal region of catheter 538 and sheath 436 surrounds and constrains AV shunt assembly 100 in the radially-compressed delivery configuration. Sheath 436 also minimizes interference between AV shunt assembly 100 and the vasculature through which it is tracked to the treatment site. In one embodiment, catheter 538 may also include a retainer (not shown) which temporarily secures a proximal end of AV shunt assembly 100 onto catheter 538. For example, the retainer may include an end stent capture configuration as described in U.S. Patent Pub. 2009/0276027 to Glynn, which is hereby incorporated by reference herein in its entirety. Delivery system 432 is advanced over guidewire 330 until tubular shunt 102 is approximately centered within tissue tract TT such that first end segment 110 of shunt 102 (obscured from view in FIG. 4) extends into artery A and the second end segment 114 of shunt 102 (obscured from view in FIG. 4) extends into vein V. In one embodiment, shunt 102 and/or anchor stents 120 my include one or more radiopaque markers (not shown) such that the relative positions thereof may be viewed under fluoroscopy as AV shunt assembly 100 is being positioned within the tissue tract TT. To aid visualization under fluroscopy, radiopaque markers can be located on the delivery system 432, for example at the distal and proximal ends of the shunt and at the midpoint of the shunt so that prior to deployment of the shunt, its location in the vessel(s) can be confirmed. In addition radiopaque markers, such as gold, tantalum, etc., can be affixed onto the shunt 102, either by crimping to the nitinol structure or sewn on the graft material such that the position of the shunt post implantation can be confirmed. Although FIG. 4 illustrates delivery system 432 being delivered through artery A and into vein V, it will be understood by one of ordinary skill in the art that the delivery system may be delivered through vein V and into artery A.

Referring now to FIG. 5, when AV shunt assembly 100 is positioned as desired, sheath 436 is proximally retracted in order to permit AV shunt assembly 100 to radially expand or deploy. More particularly, anchor stents 120 are released by retracting sheath 436 by a sufficient amount that shunt end segment 114 is exposed. Anchor stents 120 will self-expand radially outwardly relative to sheath 436 in which they were constrained. FIG. 5 shows sheath 436 retracted a sufficient amount to allow anchor stents 120 surrounding shunt end segment 114 and released support stents 118 of tubular shunt 102 to self-expand to their respective expanded diameters, i.e. expanded diameter $D_A$ and expanded diameter $D_S$. Anchor stents 120 mounted at shunt end segment 114 radially self-expand against a vessel wall of vein V and tubular shunt 102 radially expands to its expanded diameter which in an embodiment is between 25% and 75% of the luminal diameter of vein V. As shown, anchor stents 120 radially offset or position shunt end segment 114 to one side of vein V. As a result, shunt end segment 114 is oriented parallel to the wall of vein V and blood flow BF may continue through vein V with minimal obstruction. By contrast, if shunt end segment 114 were positioned diagonally across the lumen of vein V, it would present a greater obstruction and disruption of blood flow, tending to cause flow turbulence and eddy currents, which can lead to thrombus formation.

Sheath 436 continues to be proximally retracted, exposing and deploying the remaining stents 118 of tubular shunt 102 and anchor stents 120 mounted about shunt end segment 110. Proximal retraction of sheath 436 continues until a proximal inlet end 101 of AV shunt assembly 100 is exposed and allowed to radially self-expand. Catheter 538 can be withdrawn proximally through fully expanded AV shunt assembly 100 and entire delivery system 432 can then be retracted from the patient, leaving the expanded AV shunt assembly 100 deployed as shown in FIG. 6. The expanded AV shunt assembly 100 creates a blood flow passageway or connection between artery A and vein V, with blood flow entering tubular shunt 102 from artery A via inflow end 101 and blood flow exiting tubular shunt 102 into vein V via outflow end 103. As shown, anchor stents 120 extending from shunt end segment 110 radially expand against a vessel wall of artery A and radially offset or position the shunt end segment to one side of artery A. As a result, shunt end segment 110 is oriented parallel to the artery wall and some blood flow BF may continue to flow through artery A with minimal obstruction. Since tubular shunt 102 has an expanded diameter that is less than the luminal diameters of artery A and vein V, the shunt 102 essentially divides the vessel lumen into side-by-side fluid passageways. In addition, the longitudinal orientation of first and second end segments 110, 114 within artery A and vein V, respectively, directs the fluid flow into and out of the fluid passageway of the shunt and thus serves to improve the hemodynamics of blood flow through the shunt.

Figure 7:
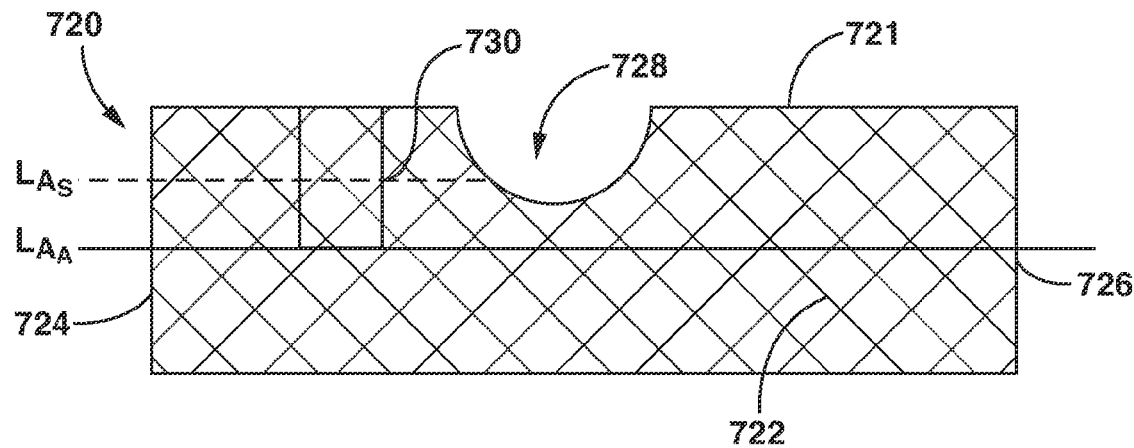
FIG. 7 is a side view of an anchor stent for use with an AV shunt according to another embodiment hereof.
Figure 8:
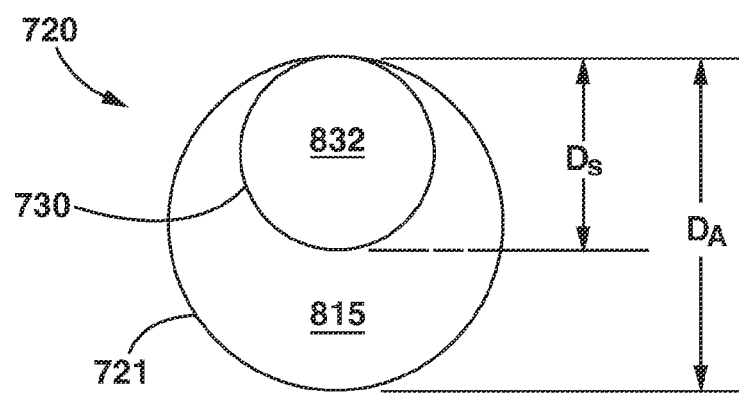
FIG. 8 is an end view of the anchor stent of FIG. 7.
Figure 9:
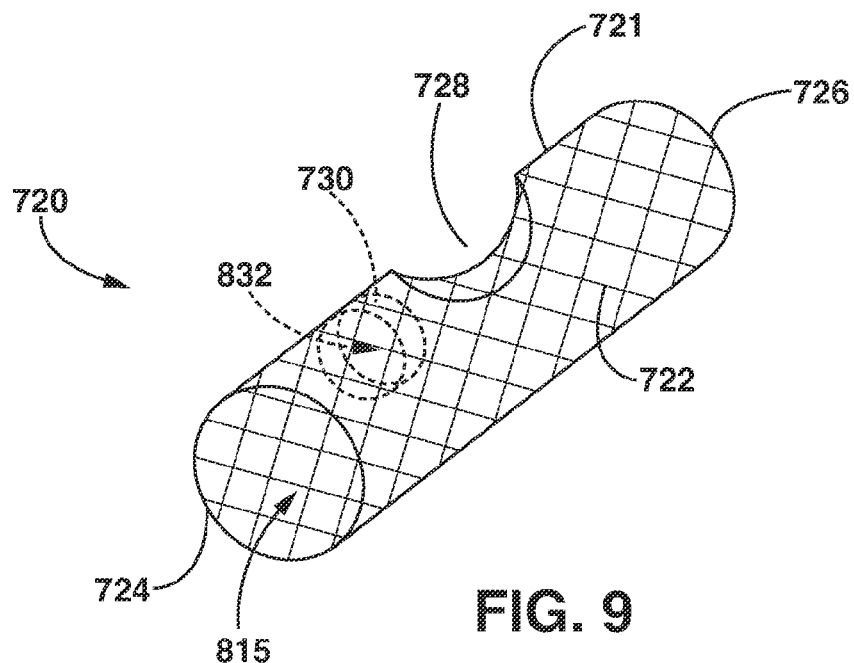
FIG. 9 is a perspective view of the anchor stent of FIG. 7.

FIGS. 7, 8 and 9 illustrate side, end, and perspective views, respectively, of an expanded anchor stent for an AV shunt assembly according to another embodiment hereof. In this embodiment, an anchor stent 720 includes a self-expanding tubular body 721 that defines a hollow bore 815 between a first open end 724 and a second open end 726 thereof. Depending on the orientation of anchor stent 720 in situ, first and second ends 724, 726 may be inflow or outflow ends of the anchor stent. Anchor stent 720 has a longitudinal axis $LA_A$. Tubular body 721 is formed from a self-expanding elastic or superelastic material, such as a nickel-titanium alloy (Manor), such that tubular body 721 tends to return to an expanded deployed configuration from a compressed or constrained delivery configuration. Radially compressible tubular body 721 of anchor stent 720 may be formed as any known self-expanding stent structure such as a wireform, an etched lattice or a woven mesh 722, and is biased to expanded diameter $D_A$, which is sized such that anchor stent 720 expands into apposition with the interior wall of a target vessel.

Anchor stent 720 includes a side port or opening 728 formed through mesh 722 of tubular body 721, and opening 728 is sized to receive AV shunt 1002 (FIG. 10) having an expanded diameter $D_S$. Anchor stent 720 also includes a retainer ring 730 defining a bore 832 for receiving and securing an end of AV shunt 1002 within the anchor stern. Retainer ring 730 may be constructed similarly to any of stents 118, 120, 720. Accordingly, the inner diameter of an expanded or deployed retainer ring 730 is approximately equal to the expanded diameter $D_S$ of shunt 1002 and an expanded outer diameter which is less than an expanded diameter of the anchor stent tubular body 721. Retainer ring 730 is coupled to an inside surface of tubular body 721 via any suitable mechanical method such as but not limited to welding or soldering, and radially extends into bore 815 of tubular body 721. Retainer ring 730 is positioned between side opening 728 and first end 724 of tubular body 721, and since at least a portion of AV shunt 1002 passes through retainer ring 730, the distance between retainer ring 730 and side opening 728 may be selected to accommodate a length of the AV shunt received there through. In addition, retainer ring 730 is aligned with opening 728 so that an AV shunt coupled to anchor stent 720 extends between retainer ring 730 and opening 728 along one side of bore 815.

When utilized to anchor and position an AV shunt, one anchor stent 720 is deployed in an artery A and one anchor stent 720 is deployed in a vein V as shown in FIG. 10. For sake of convenience, the anchor stent deployed in artery A will herein be referred to as anchor stent 720A and the anchor stent deployed in vein V will herein be referred to as anchor stent 720V although anchors 720A, 720V may be identical structures. Anchor stent 720A is delivered and deployed within artery A, e.g. by delivery device 432 such that tubular body 721A thereof expands into apposition with artery A and opening 728A is oriented towards adjacent vein V or aligned with tissue tract TT, if such has already been formed by a separate tissue penetrating catheter device (not shown) as would be known to one of skill in the art. Similarly, anchor stent 720V is delivered and deployed within vein V, e.g. by the same or different delivery device 432 such that tubular body 721V thereof expands into apposition with vein V and opening 728V is oriented towards adjacent artery A or aligned with tissue tract TT, if present. In one embodiment, anchors 720A, 720V may include one or more radiopaque markers (not shown) such that the relative positions and angular orientation thereof may be viewed under fluoroscopy as the anchors are being positioned. The radiopaque markers can be made from materials such as gold, tantalum, etc. and can be either sewn onto the graft material or joined to the nitinol frame. In particular using radiopaque markers on the retainer rings 730 will aid alignment of the shunt 1002 into each ring.

Once anchor stents 720A, 720V are in place, if tissue tract TT was not pre-formed, then a penetrating catheter such as the above-mentioned PIONEER catheter can be used to create a new tract extending between respective openings 728A, 728V of deployed anchor stents 720A,720V. Guidewire 330 is positioned through tissue tract TT, as described above with respect to FIG. 3. Then, by guiding delivery device 432 over guidewire 330, a tubular shunt 1002 is threaded through retainer ring 730A of anchor stent 720A, through opening 728A of anchor stent 720A, through tissue tract TT, through opening 728V of anchor stent 720V, and through retainer ring 730V of anchor stent 720V. Alternatively, tubular shunt 1002 can be threaded in the opposite direction, i.e. from vein V through deployed anchor stents 720V, 720A into artery A.

Tubular shunt 1002 is similar to tubular shunt 102 except that it does not include pre-mounted anchor stents 120 since anchor stents 720A, 720V are utilized for securing the shunt in place. Tubular shunt 1002 is a cylindrical stent graft that defines a fluid passageway there through, and may include graft material 1004 and a plurality of radially compressible stents 1018 attached thereto. Tubular shunt 1002 is self-expanded into securement within retainer rings 730A, 730V of anchor stents 720A, 720V, respectively, via an interference fit and thus forms a fistular conduit that is smaller than the luminal diameters of artery A and vein V. Retainer rings 730A, 730V orient first and second end segments 1010, 1014 of tubular shunt 1002 to extend parallel to the walls of artery A and vein V, respectively. Accordingly, some blood flows through shunt 1002 and the remaining blood flows through the artery A and vein V with minimal obstruction. Anchor stents 720A, 720V radially offset tubular shunt 1002 within each of artery A and vein V, respectively, and essentially divide each vessel lumen into side-by-side fluid passageways.

In the embodiment of FIG. 10, first and second end segments 1010, 1014 of shunt 1002 extend through or beyond retainer rings 730A, 730V of anchors 720A, 720V, respectively. A plurality of stents 1018 are incorporated into shunt 1002 to ensure that the body and ends of tubular shunt 1002 are prevented from collapsing. However, it will be understood by those of ordinary skill in the art that other positions of shunt 1002 within retainer rings 730A, 730V of anchor stents 720A, 720V are possible. For example, the ends of shunt 1002 may be positioned within retainer rings 730A, 730V of anchor stents 720A, 720V.

Tubular shunts described herein may include a flow control mechanism or valve that allows a physician to selectively adjust or control the blood flow through the AV shunt in situ. Adjustments of the flow may be necessary to see positive effects/improvement in the patient's condition, i.e., to maximize blood oxygenation in the treatment of COPD. Further, having the ability to adjust the volume of flow post creation of the AV shunt gives the physician the ability to make performance adjustments over time without removing the shunt. For example, FIG. 11 illustrates a tubular shunt 1102 that includes graft material 1104 and a plurality of radially compressible stents 1118 attached thereto, i.e. a stent graft. A magnetic valve 1150 is disposed within the fluid passageway of tubular shunt 1102 for selectively controlling flow through the shunt. In an embodiment, magnetic valve 1150 may be externally adjusted over a wide range of flow rates via an electromagnetic field as described in U.S. Patent Pub. No, 2010/0056978 to Machan et al., which is herein incorporated by reference in its entirety. More particularly, a strong magnetic pulse may be applied to the patient's body area in which the valve is located to cause a part within the valve to move, affecting the volume of flow permitted there through. Reversing the effect may be accomplished by applying an opposite magnetic field or applying a magnetic field at a different position. In other embodiments, suitable magnetic valves that may be utilized as valve 1150 include those described in U.S. Pat. No. 5,167, 615 to East et al.; U.S. Pat. No. 5,637,083 to Bertrand et al.; U.S. Pat. No. 5,643,194 to Negre; and U.S. Pat. No. 7,128,750 to Stergiopulos, the disclosures of which are each herein incorporated by reference in their entirety.

FIG. 12 illustrates another embodiment of a flow control mechanism or valve that allows a physician to selectively adjust or control the flow through the shunt in situ. FIG. 12 illustrates a tubular shunt 1202 that includes graft material 1204 and a plurality of radially compressible stents 1218 attached thereto, i.e. a stent graft. A cuff 1250 that may be used to reduce an inner diameter of shunt 1202 is disposed around an outer surface of tubular shunt 1202 for selectively controlling flow through the shunt. In an embodiment, cuff 1250 may be selectively inflatable in order to adjust the volume of flow permitted through the fluid passageway of shunt 1202 as described in U.S. Pat. No. 5,662,711 to Douglas; U.S. Pat. No. 6,053,891 to Decampli; U.S. Pat. No. 7,588,551 to Gertner; and WO 2009/152488 to Wu, the disclosures of which are each herein incorporated by reference in their entirety.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. An arteriovenous shunt assembly comprising:
   a tubular shunt defining a fluid passageway between open first and second ends thereof, the tubular shunt having a first end segment for placement in a first vessel, the first shunt end segment having an outer diameter smaller than a lumen diameter of the first vessel;
   a first self-expanding anchor stent having an expanded diameter greater than an expanded diameter of the tubular shunt, the first anchor stent being eccentrically coupled about the first shunt end segment such that in an expanded configuration a longitudinal axis of the first shunt end segment is parallel to and radially offset in a first direction from a longitudinal axis of the first anchor stent;
   a second shunt end segment for placement in a second vessel, the second shunt end segment having an outer diameter smaller than a lumen diameter of the second vessel; and
   a second self-expanding anchor stent having an expanded diameter greater than an expanded diameter of the tubular shunt, the second anchor stent being eccentrically coupled about the second shunt end segment such that in an expanded configuration a longitudinal axis of the second shunt end segment is parallel to and radially offset in a second direction from a longitudinal axis of the second anchor stent, wherein the second offset direction is substantially opposite the first offset direction.

2. The arteriovenous shunt assembly of claim 1, wherein the tubular shunt includes graft material mounted about a plurality of self-expanding support stents.

3. The arteriovenous shunt assembly of claim 2, wherein the first and second end segments each include at least one radially compressible support stent adjacent to the respective end of the tubular shunt.

4. The arteriovenous shunt assembly of claim 1, wherein the expanded diameter of the tubular shunt is between 25% and 75% of the expanded diameter of each anchor stent.

5. The arteriovenous shunt assembly of claim 4, wherein the expanded diameter of the tubular shunt is approximately 50% of the expanded diameter of each anchor stent.

6. The arteriovenous shunt assembly of claim 1, wherein the tubular shunt includes a flow control valve.

7. The arteriovenous shunt assembly of claim 1, wherein the first anchor stent includes a first circumferential portion tangentially coupled to the tubular shunt.

8. The arteriovenous shunt assembly of claim 1, further comprising a third anchor stent eccentrically coupled about the first shunt end segment and longitudinally spaced from the first anchor stent.

9. The arteriovenous shunt assembly of claim 1, wherein the first anchor stent includes:
   a self-expanding tubular body defining a hollow bore therethrough and having a side opening formed within a wall thereof, the side opening being sized to receive the tubular shunt therethrough; and
   a retainer ring mounted against the wall within the bore of the tubular body, wherein the retainer ring is positioned between the side opening and a first end of the tubular body;
   wherein the retainer ring has an expanded inner diameter that is sized to receive and secure the tubular shunt therewithin.

* * * * *